United States Patent [19]

Masaoka et al.

[11] Patent Number: 4,587,352
[45] Date of Patent: May 6, 1986

[54] URETHANE (METH)ACRYLATE COMPOUNDS

[75] Inventors: Yoshiji Masaoka; Motonobu Kubo, both of Iwakuni, Japan

[73] Assignee: Sanyo-Kokusaku Pulp Co., Ltd., Tokyo, Japan

[21] Appl. No.: 746,314

[22] Filed: Jun. 19, 1985

[30] Foreign Application Priority Data

Jul. 16, 1984 [JP] Japan ................ 59-147133

[51] Int. Cl.$^4$ ............................................ C07D 319/00
[52] U.S. Cl. ..................................... 549/335; 526/266
[58] Field of Search ....................... 549/335; 526/266

*Primary Examiner*—Paul R. Michl
*Attorney, Agent, or Firm*—Oblon, Fisher, Spivak, McClelland & Maier

[57] ABSTRACT

A novel urethane (meth)acrylate compound represented by a general formula shown below.

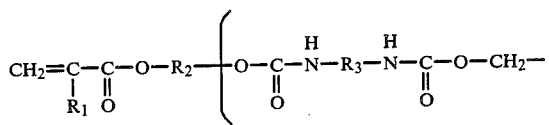

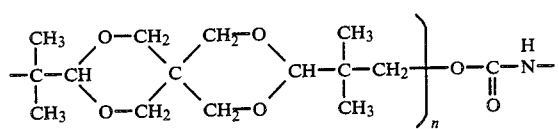

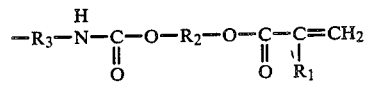

1 Claim, 1 Drawing Figure

URETHANE (METH)ACRYLATE COMPOUNDS

DETAILED DESCRIPTION OF THE INVENTION

A. Utilizable field in the industry

The present invention relates to a novel urethane (meth)acrylate compound which can be obtained advantageously by allowing (meth)acrylate to react with a reaction product of diisocyanate with spiro glycol. In more detail, the compounds of the invention have a rapid curability and are able to form cured films excellent in the hardness, toughness and adhesion. Therefore, the invention concerns the novel radically-polymerizable urethane compounds useful for the forming material of paint film, casting material, blockading agent, molding material, sealing material, etc.

B. Conventional techniques

The reaction products between spiro glycol and diisocyanate are described in the specification of U.S. Pat. No. 2,945,008, but these reaction products do not contain the (meth)acryloyl group. Accordingly, these are different substantially from the compounds of the invention.

Also, in the publications such as Japanese Patent Publication No. 8013/1980, Japanese Unexamined Patent Publication No. 165422/1982 and Japanese Unexamined Patent Publication No. 219214/1983, there are descriptions with regard to urethane (meth)arcylate. However, in these, urethane (meth)acrylates containing spirane nucleus

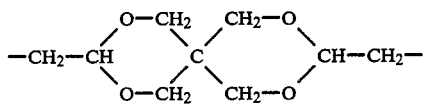

are not described in any way showing a substantial difference from the compounds of the invention.

C. Problems to be solved by the invention

Recently, the photocurable resins are used widely for the paint, ink, adhesive, resist, etc. This is because that the photocurable resins have been recognized to have such advantages as disuse of solvent for paint film, shortening of cure time and extension of tank life of resin and to make the energy conservation, labor saving and pollution freeing which are requests of the times possible.

Currently, the so-called prepolymers, which are unsaturated compounds of high molecular weight, used for the principal ingredient of the photocurable resin are classified roughly into four types of unsaturated polyester, epoxy (meth)acrylate, urethane (meth)arcylate and (meth)acrylate of various esters. Above all, urethane (meth)acrylates are very promising also in future due to the facts that the tough paint film can be obtained through the intermolecular forces of urethane group, that the adhesion and the processibility are also excellent, and the like.

Actually, in the case of the manufacture of urethane (meth)acrylates, a variety of modifications is possible through the reactivity of isocyanate group and, by utilizing this, the improvement meeting various needs can be expected in the physical properties.

D. Means to solve the problems

In view of the situations as these, the inventors have come to invent the novel urethane (meth)acrylate compounds represented by a general formula (I) shown below.

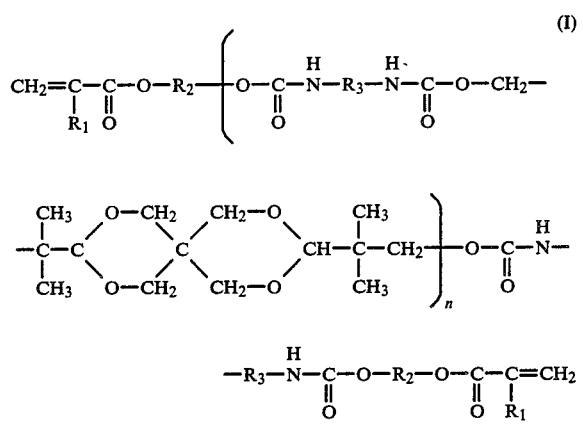

[wherein, R, indicates —H or —CH$_3$, R$_2$ indicates an alkylene group having carbon atoms of 1 to 6 with or without side chains or —(—CH$_2$CH$_2$—O—)$_m$—CH$_2$CH$_2$—, m=1-5, R$_3$ indicates a substituent selected from a group comprising

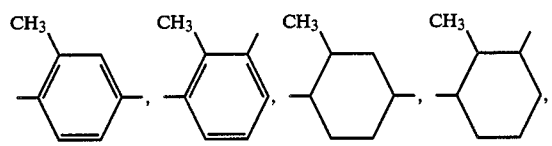

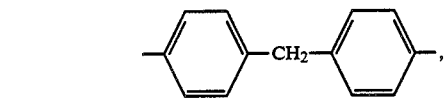

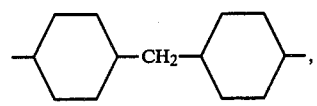

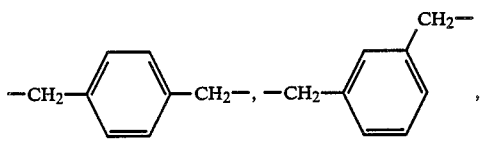

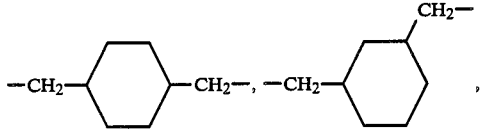

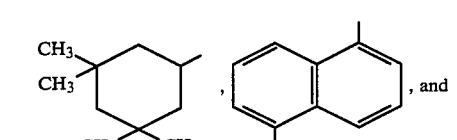

-continued

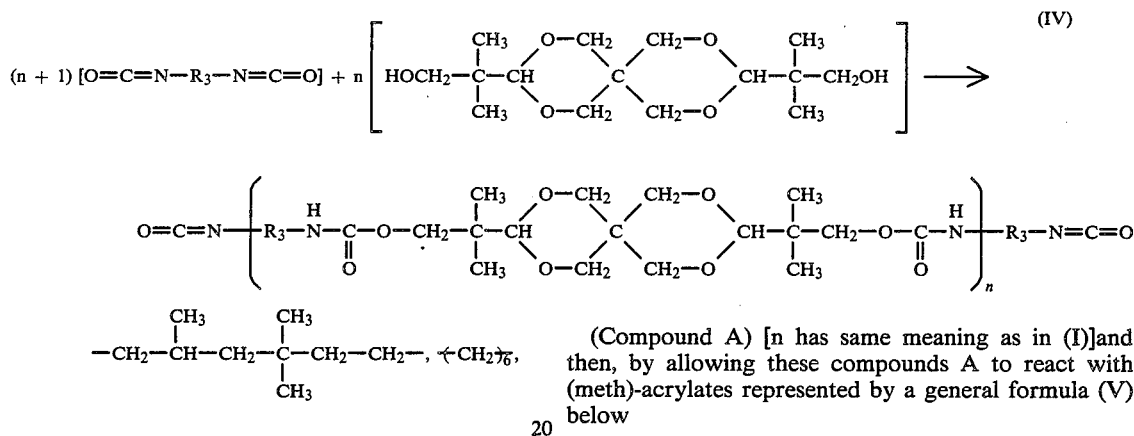

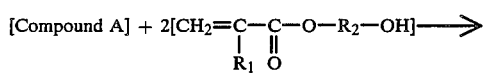

and n is a number selected among intergers of 1 to 10 so as the molecular weight of compound to be less than 5000].

E. Action and effect

In addition to the capability of forming the cured films excellent in the hardness, toughness and adhesion through urethane linkage, these compounds are expected to be excellent also in the weatherability and tracking resistance because of the presence of spirane nucleus

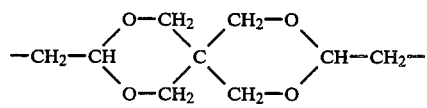

The urethane (meth)acrylate compounds of the invention are manufactured by allowing, for example, diisocyanates represented by a general formula (II)

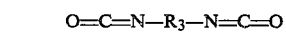    (II)

to react with sprio glycol represented by (III)

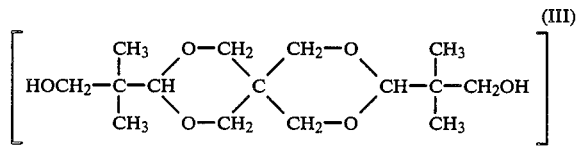    (III)

in the way shown below to prepare compounds A represented by a general formula (IV)

(Compound A) [n has same meaning as in (I)]and then, by allowing these compounds A to react with (meth)-acrylates represented by a general formula (V) below $$CH_2=C-C-O-R_2-OH \quad (V)$$
$$\phantom{CH_2=}R_1 \phantom{-C-}O$$

in the way shown below.

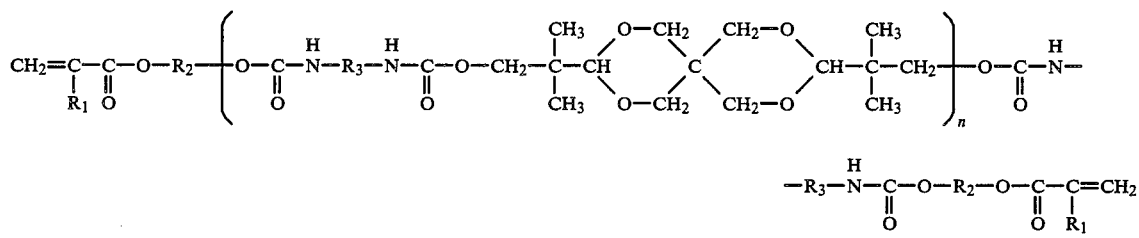

The reaction between diisocyanates of the general formula (II) and spiro glycol of (III) described above progresses by using the metallic compounds such as dibutyl tin dilaurate etc. or the catalysts such as tertiary amine etc. As the typical polymerization inhibitors of (meth)acrylates, there are hydroquinone monomethyl ether (MEHQ) etc. The reaction can be conducted without solvent or, if necessary, with solvent compatible with the product.

The reason why the molecular weight of urethane (meth)-acrylates thus obtainable was kept less than 5000 is due to a fact that the function as prepolymer was hard to be accomplished if more than 5000.

F. Examples

In following, examples will be shown.

EXAMPLE 1

In a four-neck flask of 1 liter fitted with thermometer, reflux condenser and stirrer were placed 261 g (1.5 mol) of tolylenediisocyanate (TDI) [made by Tokyo Chemicals Co.], 304 g (1.0 mol) of spiro glycol [made by Mitsubishi Gas Chemistry Co.] and 500 ml of tetrahydrofuran. Then, 0.2 g of dibutyl tin dilaurate were added and the mixture was heated. Heat was evolved at the same time with the initiation of reaction, but the maximum temperature during the reaction remained at 72° C. After ceased the temperature rise resulting from exothermic reaction, stirring was continued for about 2 hours at 60° C. To the product obtained were added 0.02 g of hydroquinone monomethyl ether (MEHQ) and 116 g (1.0 mol) of 2-hydroxyethyl acrylate (HEA). At this time, the maximum temperature during the reaction was also 70° C. After ceased the evolution of heat, stirring was continued further for about 1 hour at 60° C. THF was distilled off by using evaporator, and the product obtained was subjected to the vacuum drying (5 mmHg) for 3 hours at 40° C. to obtain pale yellow substance 1 in the solid form.

The interpretation of IR spectrum with this pale yellow substance (FIG. 1) revealed as follows:

| 3330 cm$^{-1}$ | Absorption due to the stretching vibration of N—H |
| 2960 cm$^{-1}$ <br> 2830 cm$^{-1}$ | Stretching vibration of aliphatic C—H |
| Near 1720 cm$^{-1}$ | C=O of urethane bond and ester bond of acryloyl group |
| 1610 cm$^{-1}$ <br> 1590 cm$^{-1}$ | Stretching vibration of C=C in benzene nucleus |

The absorption of isocyanate group at 2270 cm$^{-1}$ was entirely not found. Moreover, the number of peaks was observed to be three from gel permeation chromatography (GPC), and TDI which was unreacted monomer, spiro glycol and HEA were entirely not detected. The softening temperature was 51° to 52° C.

Therefore, this pale yellow substance 1 was found to be

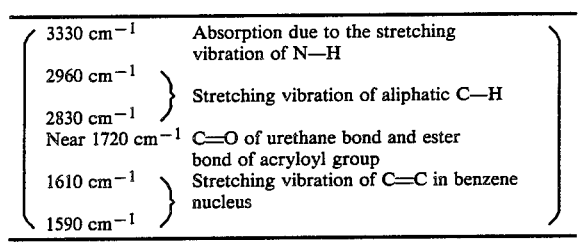

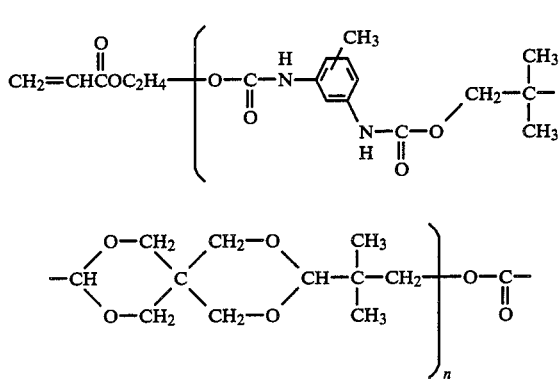

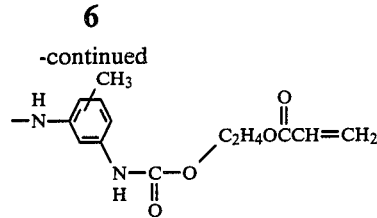

n = 1,2,3

*Analytical instruments

Infrared spectrophotometer: Nihon Spectrum Co., IRA-1

Measurement apparatus of gel permeation: Toyo Soda Industries Co., HLC-802UR Measured with THF (2% solution)

EXAMPLE 2

Except that tolylenediisocyanate in Example 1 was replaced by hexamethylenediisocyanate, the reaction was conducted similarly to that in Example 1. As a result, white substance 2 was obtained in the solid form, which showed a melting point 85° to 86° C.

After made similar analysis to that in Example 1, this white substance 2 was found to have following structure.

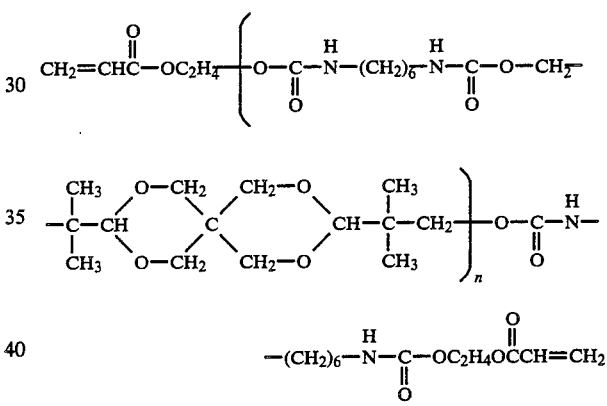

n = 1,2,3,4

EXAMPLE 3

Except that tolylenediisocyanate in Example 1 was replaced by 4,4'-diphenylmethanediisocyanate (MDI), the reaction was conducted similarly to that in Example 1. As a result, pale yellow substance 3 was obtained in the solid form, which showed a melting point of 75° to 76° C.

After made similar analysis to that in Example 1, this pale yellow substance 3 was recognized to have following structure.

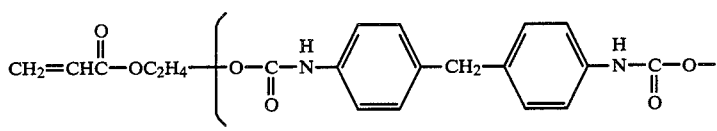

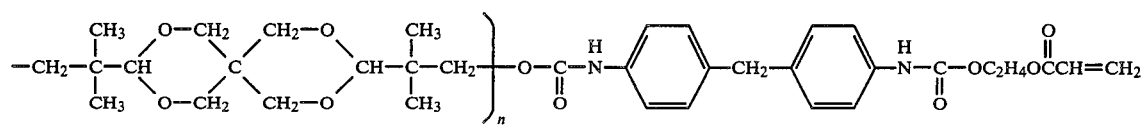

n = 1,2,3,4

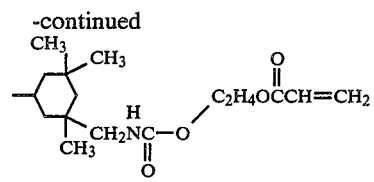

n = 1,2,3

EXAMPLE 4

Except that tolylenediisocyanate in Example 1 was replaced by isophoronediisocyanate (IPDI), the reaction was conducted similarly to that in Example 1. As a result, white substance 4 was obtained in the solid form, which showed a melting point of 49° to 50° C.

After made similar analysis to that in Example 1, this white substance 4 was recognized to have following structure.

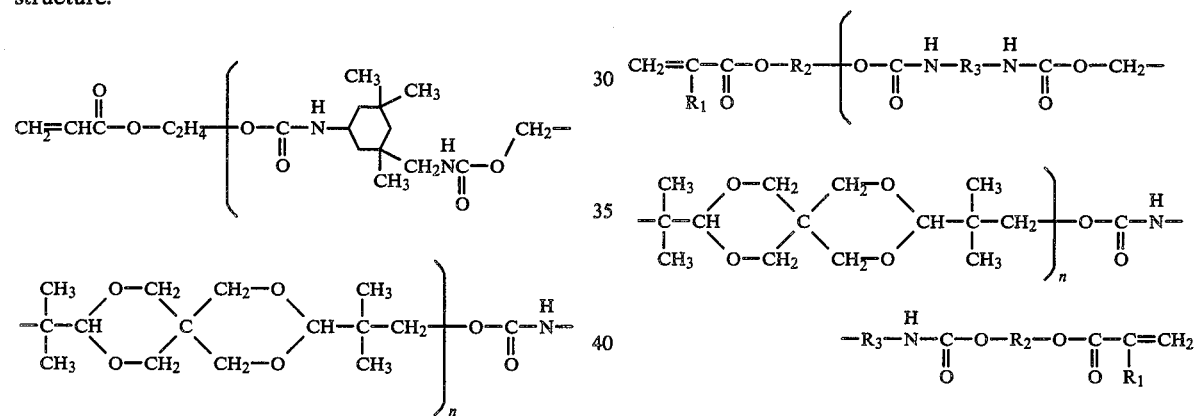

Figure 1:
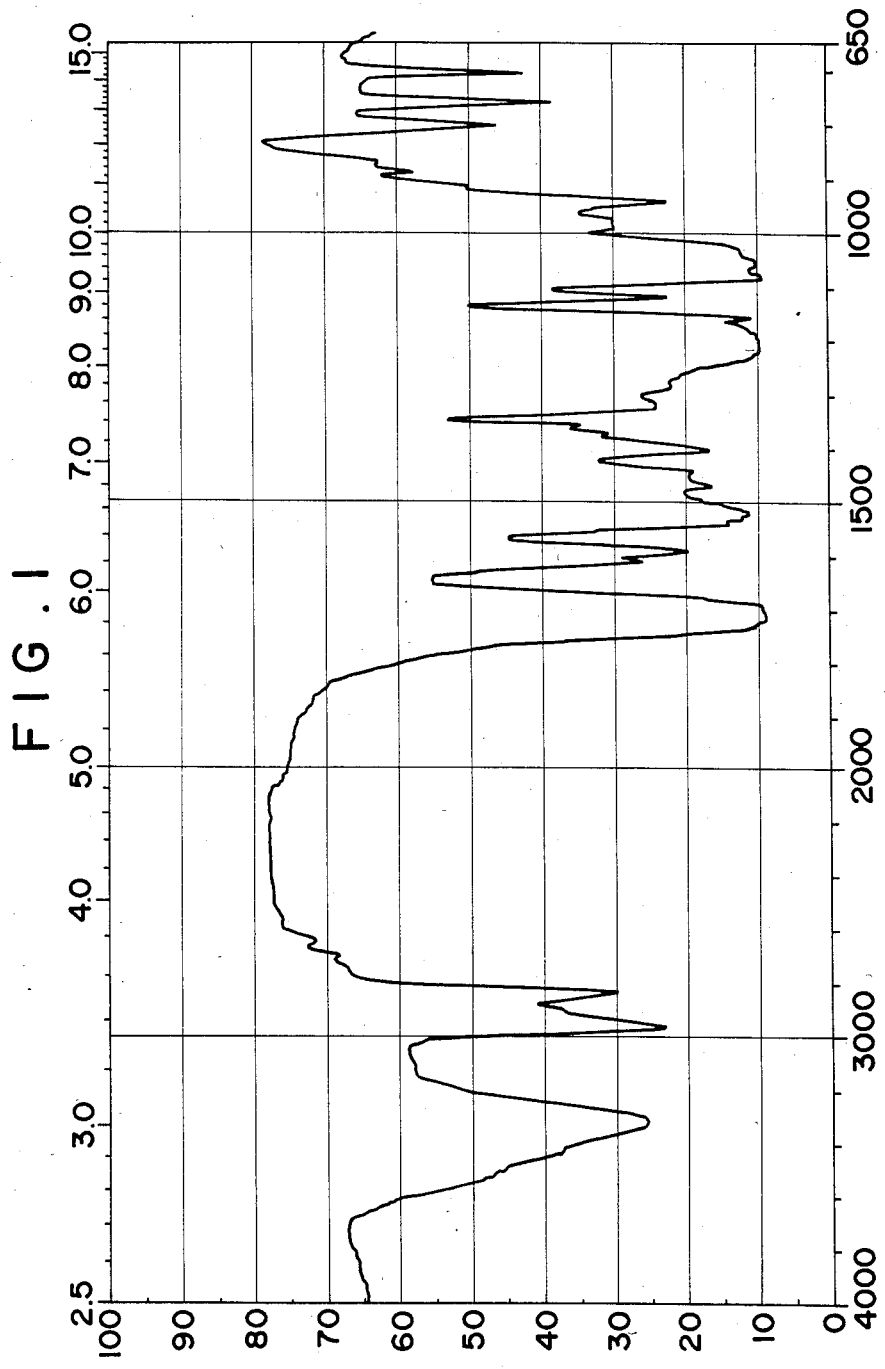
FIG. 1 is a diagram showing IR spectrum of the substance 1 of the invention obtained in Example 1 of the invention.

What is claimed is:

1. A novel urethane (meth)acrylate compound represented by a general formula shown below.

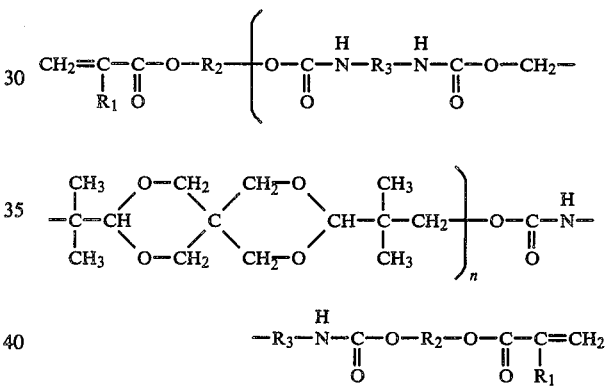

* * * * *